United States Patent [19]

Difiglio et al.

[11] 4,101,284
[45] Jul. 18, 1978

[54] MULTIPLE BEAD DISPENSER FOR DIAGNOSTIC ASSAY

[75] Inventors: Joseph J. Difiglio, Vernon Hills; Richard W. George, Libertyville, both of Ill.

[73] Assignee: Abbott Laboratories, North Chicago, Ill.

[21] Appl. No.: 844,667

[22] Filed: Oct. 25, 1977

[51] Int. Cl.² .................. G01N 33/16; B65G 65/60
[52] U.S. Cl. .................................. 23/259; 221/95; 221/264
[58] Field of Search ............... 23/259, 253 R, 230 B; 195/127; 141/319–322; 221/93, 95, 137, 263, 264; 222/361–363

[56] References Cited

U.S. PATENT DOCUMENTS

| | | |
|---|---|---|
| 2,865,156 | 12/1958 | Wolfson .................... 221/93 X |
| 3,417,542 | 12/1968 | Merrill et al. .............. 221/93 X |
| 3,843,450 | 10/1974 | Saxholm .................... 23/230 R |
| 3,932,141 | 1/1976 | Beall et al. ................ 23/253 R |
| 3,963,456 | 6/1976 | Tsuchiya et al. .......... 221/264 X |

Primary Examiner—R.E. Serwin
Attorney, Agent, or Firm—Neal O. Willmann; Robert L. Niblack

[57] ABSTRACT

This invention relates to an apparatus which is useful for dispensing simultaneously a plurality of beads into any multi-well container suitable for the performance of diagnostic assays.

4 Claims, 6 Drawing Figures

MULTIPLE BEAD DISPENSER FOR DIAGNOSTIC ASSAY

BACKGROUND OF THE INVENTION

There is increasing popularity in the use of solid supports to aid in conducting immunologic assays. Solid supports, referred to hereinafter as beads, have certain advantages over some of the other support forms which have been used previously in immunodiagnostic assays. Beads, fashioned from glass, metal or any plastic material such as polystyrene, polyurethane, polypropylene and the like can be coated with various absorbents such as resins, clays, charcoals, silica gels and the like to facilitate absorbing and separating the components of biochemical assays. The beads can also be coated with immunoreactants and thereby participate directly in the assay reaction. After the components on the bead surface have been allowed to absorb or react, the bead can be separated easily from the reaction medium to permit a quick and accurate analysis of its surface.

The prior art requires that the beads be individually dispensed into each reaction container or well. In the situation where a large number of similar tests are being conducted at the same time, dispensing each bead individually is tedious and time consuming. The disclosed apparatus solves this problem by permitting the simultaneous dispensing of a plurality of beads into reaction wells. This apparatus also provides a closed system in which the beads can be transported from their commercial container, into the apparatus, and then to the reaction medium with a minimum risk of contamination for both the beads and the individual conducting the assay.

BRIEF SUMMARY OF THE INVENTION

This application discloses an apparatus which is particularly useful for simultaneously dispensing a plurality of beads to be used as solid supports in the performance of immunologic diagnostic assays. The device comprises a threaded container support having an opening for the delivery of beads from a container into the apparatus; a block defining a reservoir having a bottom with a plurality of vertical apertures extending downwardly from the bottom and having a cover with a portal communicating with said opening in the threaded container support; a base plate mounted beneath and peripherally on no more than three sides to said reservoir block, having a plurality of vertical apertures located in a position predetermined to be unaligned with the apertures in the bottom of the reservoir block and extending downwardly from the bottom through the base plate; a sliding plate situated between the reservoir block and the base plate and within the peripheral attachment of said block and plate having a plurality of vertical apertures located in a predetermined position to be aligned with said apertures in the bottom of the reservoir plate and extending downwardly to the surface of said base plate; and a biasing means constructed in a range to permit lateral movement of the sliding plate sufficient to align the vertical apertures in the sliding plate with those of the base plate and return the sliding plate so that its vertical apertures again align with those of said reservoir.

DESCRIPTION OF THE PREFERRED EMBODIMENTS

Figure 2:
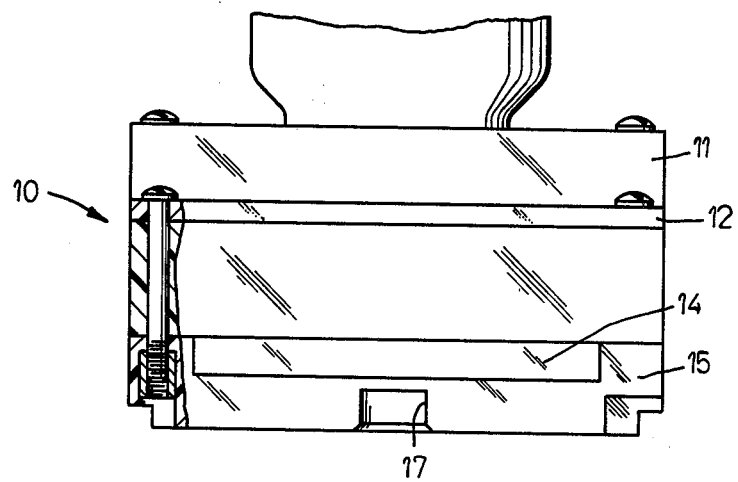
FIG. 2 is an end view of the bead dispenser with a portion broken away for the sake of clarity.
Figure 1:
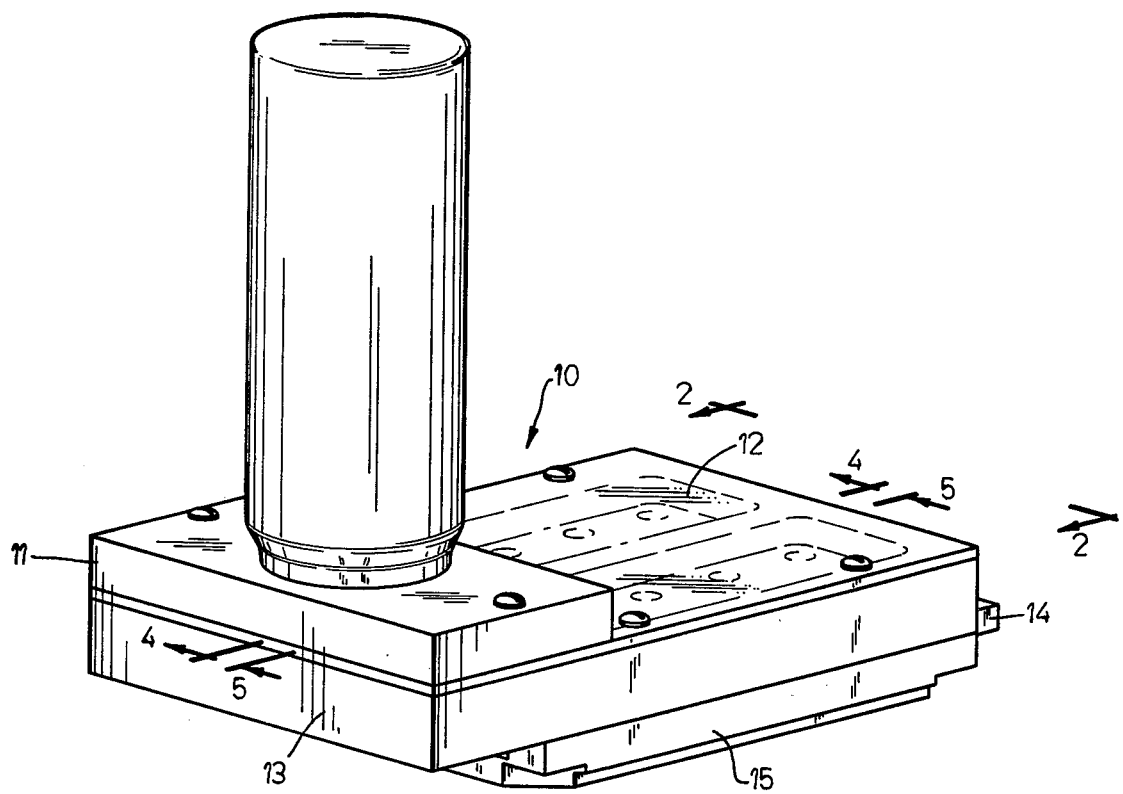
FIG. 1 is a perspective view of the bead dispenser with a container attached.
Figure 3:
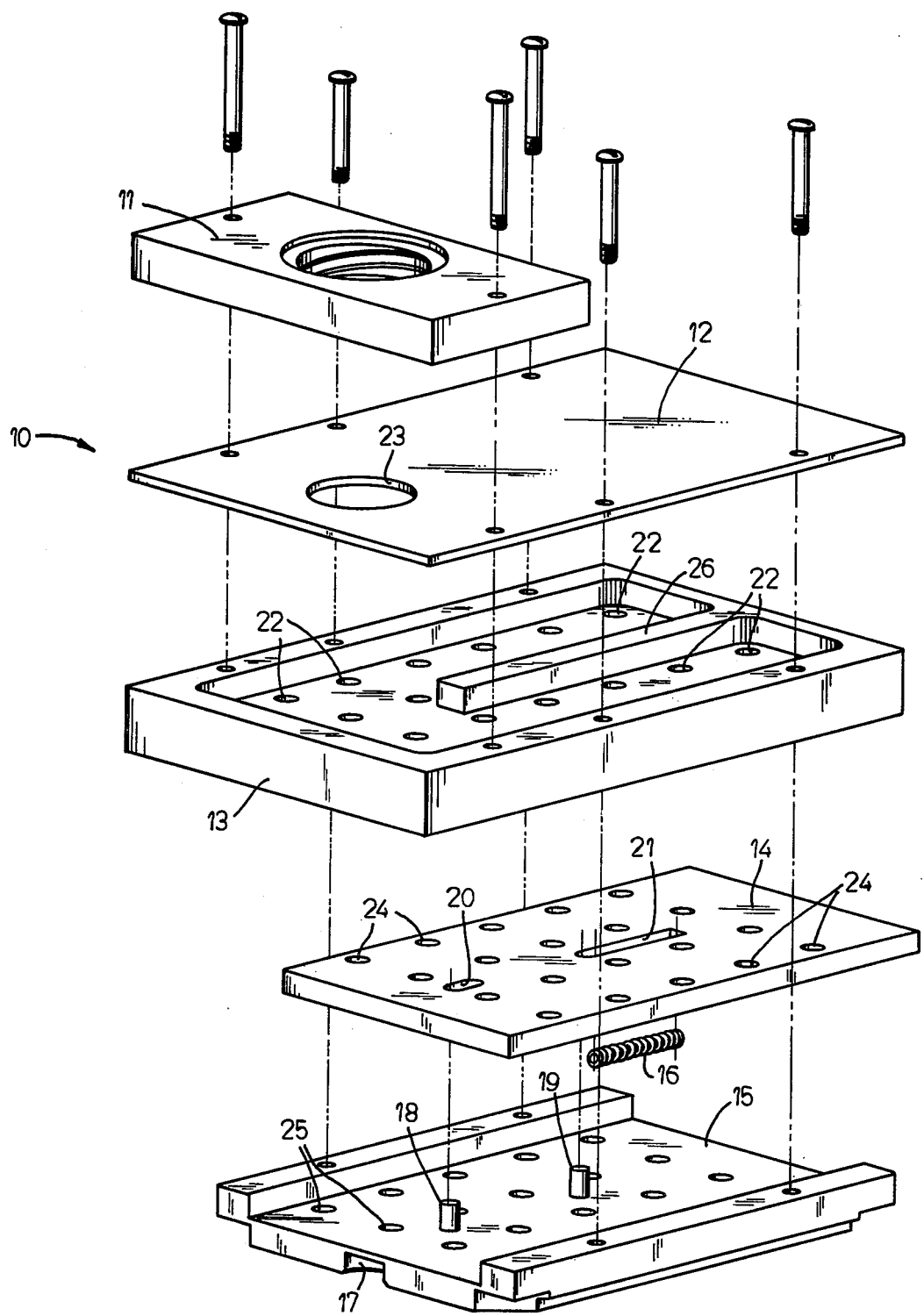
FIG. 3 is an isometric exploded view of the claimed bead dispenser.
Figure 4:
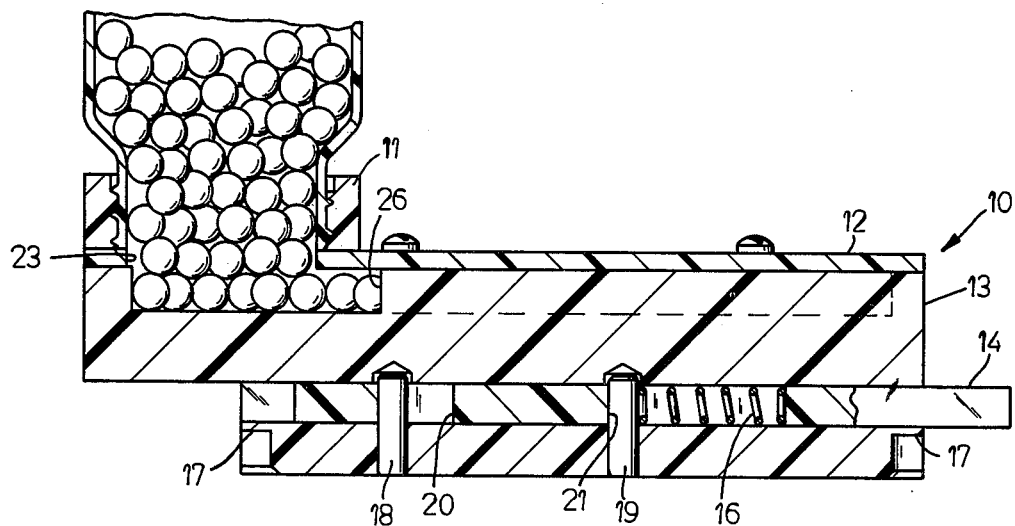
FIG. 4 is a sectional view of the bead dispenser taken on line 5.5 of FIG. 1 showing the beads entering the reservoir.
Figure 5:
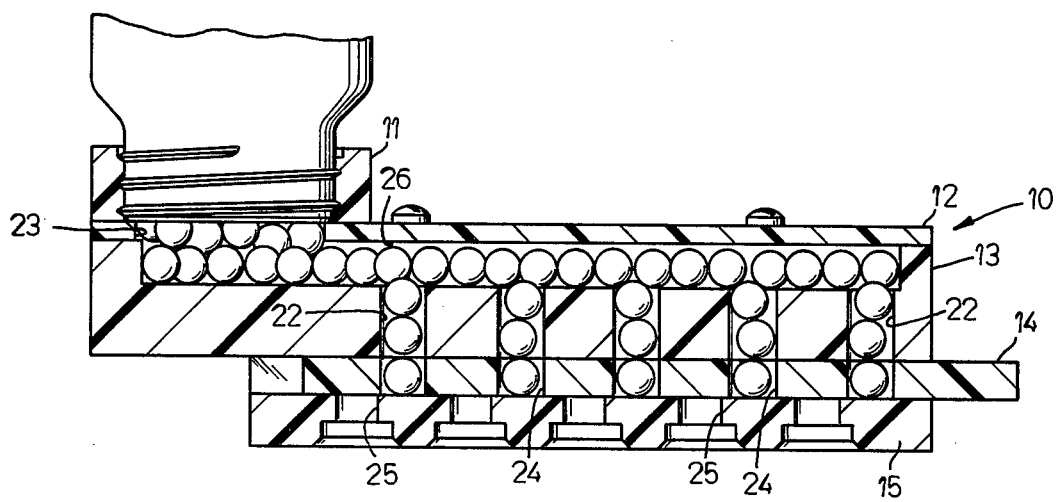
FIG. 5 is a sectional view of the bead dispenser taken on line 5.5 of FIG. 1 showing the beads descending through the vertical apertures in the bottom of the reservoir block and entering the vertical apertures of the slide plate.
Figure 6:
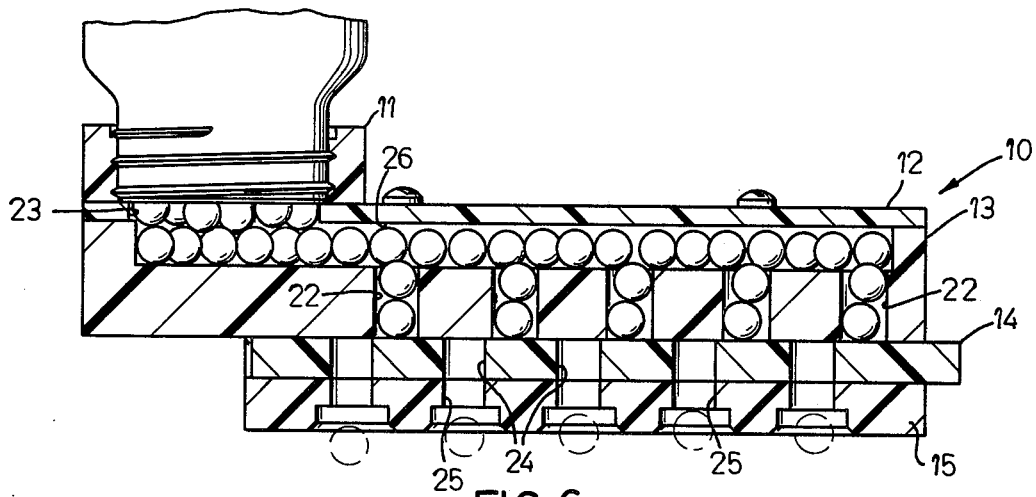
FIG. 6 is a sectional view of the bead dispenser taken on line 5.5 of FIG. 1 showing that the slide plate has been moved laterally so as to align its apertures with those in the base plate and thereby allowing the beads previously confined within the apertures of the slide plate to descend through the base plate and be dispensed.

The multiple bead dispenser has been designed to encourage the attachment of an uncapped container of beads. To facilitate this attachment the multiple bead dispenser 10 is equipped with a threaded container support 11. This support can be threaded variously to accommodate a variety of container openings. Filling the dispenser is easily accomplished by inverting the threaded support 11 over the bead container and screwing the container into the threaded support. By providing for the firm attachment of the bead container, the opportunity to contaminate or be contaminated by the various coatings or absorbed components on the beads is minimized. The threaded container support necessarily features a bead portal 23 through which the beads will descend from their container into the reservoir 13 of the apparatus. If necessary it is convenient to shake the dispenser and affixed container gently so that the beads will cascade from the bottle into the reservoir 13. The reservoir 13, as the name suggests, should accommodate a large number of beads. It has a cover 12 to contain the beads and further prevent possible contamination of either the user or the bead. In the bottom of the reservoir 13 a plurality of vertical apertures 22 are situated. These apertures are designed to receive at least one bead and align it for eventual dispensing according to the purpose of the apparatus. In order to insure that all of the vertical apertures 22 receive a bead, it is suggested that the cover 12 of the reservoir be fabricated from a transparent material. As a practical matter, the apparatus 10 is small enough to be manipulated so that if the cover 12 is transparent all vertical apertures 22 can receive at least one bead providing, of course, that the number of beads is not limited. It is recommended that the reservoir 13 be filled no more than two-thirds full. The beads cannot roll freely into the apertures 22 if the reservoir is packed.

As the bead supply diminishes, it becomes more difficult to direct the remaining beads into vertical apertures 22 needing beads to assure dispensing the maximum quantity. A preferred embodiment of the claimed apparatus 10 features a reservoir 13 having at least one rib 26 to aid in directing the alignment of beads. The rib 26 functions as a guide along which a bead may be rolled and directed to an available aperture 22.

After entering the vertical apertures 22 in the bottom of the reservoir 13, the beads will necessarily descend by gravity into pre-aligned vertical apertures 24 of the sliding plate 14. The vertical apertures 24 of the sliding plate 14 should be of a size slightly larger than the size of the bead or beads to be dispensed.

The sliding plate 14 is attached to a biasing means 16 such as a spring so that said plate can be laterally moved or manipulated so that its vertical apertures 24 can be brought into alignment with the vertical apertures 25 of the base plate 15 and returned to the resting position in which its apertures 24 align with the apertures 22 of the reservoir 13.

Applicants have achieved the proper alignment of the sliding plate 14 with both the reservoir 13 and the base plate 15 by inserting the biasing means 16 within a biasing means channel 21. This channel 21 provides an unencumbered area for allowing the biasing means to expand and contract. The expansion of the biasing means 16 and return of the sliding plate to a resting position is achieved by providing an attachment pillar 19 which is firmly secured to the base plate 15 and extends through a pillar portal 20 in the sliding plate 14.

When the apertures 24 of the sliding plate 14 are aligned with the apertures 25 of the base plate 15, any and all beads within the apertures 24 of the sliding plate 14 will descend through the apertures 25 of the base plate 15 and be dispensed into awaiting recepticals.

Applicants' multiple bead dispenser has been designed to dispense beads into reaction trays containing a predetermined number of wells. Although the total number of wells is not critical, the dispenser will perform best if the tray contains a multiple of wells several times larger than the dispenser is capable of dispensing at one time. To aid in serving this purpose the bottom of the base plate 15 can be fabricated to contain an alignment guide 17 to insure that the bead dispenser is properly positioned over a sufficient number of wells so that no beads are improperly dispensed and wasted. For example, a prototype of the multiple bead dispenser has been designed to dispense twenty beads simultaneously. This particular dispenser has been adapted to nest securely over twenty wells in a 60-well reaction tray in only three positions. After twenty wells have received their beads, the dispenser is moved along the reaction tray until the alignment guide on the bottom of the base plate secures a definite nesting position over the adjacent set of twenty wells. Any beads remaining in the apparatus after all testing has been completed may be returned to the bead container by simply inverting the apparatus and the affixed container.

The multiple bead dispenser has been designed to facilitate cleaning and maintenance. It is ideally fabricated from an inert, plastic substance so that it may be disassembled easily and thoroughly cleaned with chemical reagents so as not to contaminate subsequently used beads having different chemical properties.

What is claimed is:

1. An apparatus useful for simultaneously dispensing a plurality of beads to be used as solid supports in the performance of immunologic diagnostic assays which comprises:
   (a) a threaded container support having an opening for the delivery of beads from a container into the apparatus;
   (b) a block defining a reservoir having a bottom with a plurality of vertical apertures extending downwardly from the bottom and having a cover with a portal communicating with said opening in the threaded container support.
   (c) a base plate mounted beneath and peripherally on no more than three sides to said reservoir block, having a plurality of vertical apertures located in a position predetermined to be unaligned with the apertures in the bottom of the reservoir block and extending downwardly from the bottom through the base plate;
   (d) a sliding plate situated between the reservoir block and the base plate and within the peripheral attachment of said block and plate having a plurality of vertical apertures located in a predetermined position to be aligned with said apertures in the bottom of the reservoir plate and extending downwardly to the surface of said base plate; and
   (e) a biasing means constructed in a range to permit lateral movement of the sliding plate sufficient to align the vertical apertures in the sliding plate with those of the base plate and return the sliding plate so that its vertical apertures again align with those of said reservoir.

2. The apparatus according to claim 1 wherein the cover of the reservoir block is transparent.

3. The apparatus according to claim 1 further defined as having the capability of orienting a plurality of beads from a bulk source into a predetermined pattern.

4. The apparatus according to claim 1 wherein the biasing means is a spring.

* * * * *